United States Patent [19]

Vetter et al.

[11] 4,451,487
[45] May 29, 1984

[54] PROCESS FOR THE PURIFICATION OR ENRICHMENT OF BIOLOGICALLY ACTIVE PROTEINS

[75] Inventors: Hellmuth Vetter, Tutzing; Peter Scheibe, Munich; Waldemar Thum; Gotthilf Näher, both of Tutzing, all of Fed. Rep. of Germany

[73] Assignee: Boehringer Mannheim GmbH., Mannheim, Fed. Rep. of Germany

[21] Appl. No.: 377,277

[22] Filed: May 12, 1982

[30] Foreign Application Priority Data

May 15, 1981 [DE] Fed. Rep. of Germany ....... 3119453

[51] Int. Cl.$^3$ .............................................. C12N 9/00
[52] U.S. Cl. .................................... 435/183; 435/814
[58] Field of Search ........ 435/183, 184, 261, 814–816; 260/112 R

[56] References Cited

U.S. PATENT DOCUMENTS

| 3,098,015 | 7/1963 | Ayrapaa | 435/816 X |
| 3,580,840 | 5/1971 | Uridil | 435/261 X |
| 3,728,224 | 4/1973 | Borglum | 435/814 X |
| 3,862,901 | 1/1975 | Wennerblom et al. | 435/814 X |

Primary Examiner—Thomas G. Wyse
Attorney, Agent, or Firm—Felfe & Lynch

[57] ABSTRACT

The present invention provides a process for the purification or enrichment of biologically active proteins by the addition of a selective precipitation agent, wherein an aqueous solution containing the desired protein is mixed at a pH value below its isoelectric point with such an amount of an arylsulphonic acid azo dyestuff with two sulphonate groups, which are separated from one another by 8 to 10 double bonds standing in resonance relationship, among which there is present at least one N=N double bond, that at least the greater part of the biological activity of the desired active protein is present in the precipitate, the precipitate is separated off and the active protein is again brought into solution at a pH value above its isoelectric point.

The present invention also provides an agent for the selective precipitation of biologically active proteins from aqueous solutions thereof without the loss of the biological activity, wherein it contains or consists of an aryl sulphonic acid azo dyestuff with two sulphonate groups, which are separated from one another by 8 to 10 double bonds standing in resonance relationship, among which there is present at least one N=N double bond.

11 Claims, No Drawings

PROCESS FOR THE PURIFICATION OR ENRICHMENT OF BIOLOGICALLY ACTIVE PROTEINS

The present invention is concerned with a process for the purification or enrichment of biologically active proteins and with an agent which can be used for carrying out this process.

Several agents and processes are already known for the enrichment of biologically active proteins. Examples of such agents include salts, such as ammonium sulphate, organic solvents, such as acetone, inorganic gels, active charcoal, chromatographic exchangers, molecular sieves, polyethyleneimines and the like. Having regard to the extraordinary variety of naturally occurring active proteins and of their accompanying materials, the absence of possibilities of variation for separation or purification frequently, however, makes itself disadvantageously noticeable. Of the already limited number of processes and agents available for the purification and enrichment of proteins, most have proved to be of only very little use in special cases. The result of this is that the same purification steps must often be repeated in order to achieve a reasonably satisfactory separation from accompanying materials. The degrees of enrichment achieved are, in addition, mostly small and the subsequent removal of the agent used for the enrichment requires special measures, such as the evaporation of large volumes of liquid and the like. Therefore, the various known processes for the enrichment or purification of biologically active proteins by and large always involve the same process steps which are repeated with great similarity, even if in different order.

Therefore, there is a need for additional processes for the purification and enrichment of biologically active proteins which improve the available possibilities of variation and make the protein enrichment more effective.

Thus, it is an object of the present invention to provide a further process and agent for the purification or enrichment of biologically active proteins which impair as little as possible the biological activity of the proteins and broaden the existing possibilities of variation.

Thus, according to the present invention, there is provided a process for the purification or enrichment of biologically active proteins by the addition of a selective precipitation agent, wherein an aqueous solution containing the desired protein is mixed at a pH value below its isoelectric point with such an amount of an arylsulphonic acid azo dyestuff with two sulphonate groups, which are separated from one another by 8 to 10 double bonds standing in resonance relationship, amongst which there is present at least one N=N double bond, that at least the greater part of the biological activity of the desired active protein is present in the precipitate, the precipitate is separated off and the active protein is again brought into solution at a pH value above its isoelectric point.

It is admittedly known that many dyestuffs enter into an exchange action with proteins. However, insofar as precipitations thereby occur, the biological activity of the protein contained in the precipitation complex is normally completely lost. Surprisingly, this denaturing does not occur in the case of the above-defined azo dyestuffs and, furthermore, the precipitation of the various proteins takes place very selectively so that an excellent purification and enrichment effect is achieved. It is especially surprising that the process according to the present invention is only little dependent upon foreign salts and, therefore, can also be applied to crude cell extracts. Therefore, in many cases, it is possible selectively to precipitate the desired biologically active proteins from crude cell extracts and to separate them from the greater part of the contaminating foreign proteins and other cell extract component materials. In the same way, a direct precipitation from fermentation broths is possible. Since the sulphonic acid groups of the precipitation agent are fully ionised down to about pH 2, the pH value optimum for the precipitation depends practically exclusively upon the ionisability and the pH stability of the active protein in question. In general, the process can be used for those proteins, the biological activity of which is also still maintained below their isoelectric point. This prerequisite is, in general, given when the active protein can be adsorbed on cation exchangers without substantial loss of activity. This can be rapidly ascertained in a simple preliminary experiment.

By biologically active proteins in the sense of the present invention, there are preferably understood the enzymatically active and immunologically active proteins.

However, the process can also be used for other biologically active proteins, for example hormones, toxins, immunoglobulins and the like. Examples of enzymatically active proteins to which the process according to the present invention can be applied include ADH from liver, aldolase, α-amylase from fungi or pancreas, ascorbate oxides, bromelain, α-bungarotoxin, β-bungarotoxin, cholesterol esterase, cholesterol oxidase, carboxypeptidase-B, chymotrypsin, diaphorase, fumarase, α-galactosidase from coffee beans or from yeast, glucose-6-phosphate dehydrogenase from yeast, glutathione reductase, glycerol-3-phosphate dehydrogenase, oxalate oxidase, papain, phospholipase A2, peroxidase, penicillinamidase, 6-phosphogluconate dehydrogenase, trypsin, triose phosphate isomerase and uridine diphosphoglucose pyrophosphorylase, as well as numerous other enzymes.

According to the present invention, the azo dyestuff used is preferably 3,3'-(4,4'-biphenylylene-bis-(azo))-bis-(4-amino-1-naphthalenesulphonic acid) or a derivative thereof substituted by one or more lower alkyl or lower alkoxy groups. The compounds of this preferred group can be represented by the following general formula:

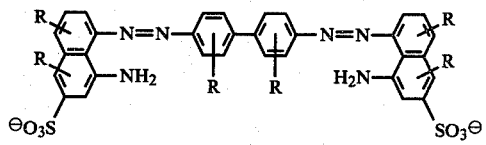

wherein each R, independently of one another, is a hydrogen atom or a $C_{1-4}$ alkyl or $C_{1-4}$ alkoxy radical.

Typical examples of this preferred group of azo dyestuffs include the commercially available dyestuffs Congo Red (C.I. 22120) and benzopurpurin 10B (C.I. 23560).

A further preferred group of azo dyestuffs consists of 2,2'-[(diazoamino)-di-p-phenylene]-bis-(7-benzothiazolesulphonic acid) and its derivatives containing one or more lower alkyl and/or lower alkoxy radicals. The compounds of this preferred group can be represented by the following general formula:

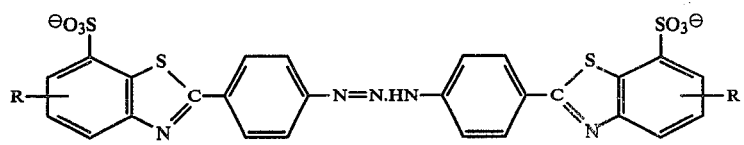

wherein each R, independently of one another, is a hydrogen atom or a $C_{1-4}$ alkyl or $C_{1-4}$ alkoxy radical.

A typical example for this preferred group is thiazole yellow G (C.I. 19540).

The dyestuff is added in dissolved form. 0.05 to 5% solutions (depending upon the solubility of the azo dyestuff in question) have proved to be well suitable but more highly diluted solutions can also be employed although, as a rule, unnecessarily too much water is thereby introduced. The appropriate amount of dyestuff depends upon the amount of protein to be precipitated. In general, it is from about 0.01 to about 2.0% wt./vol. and preferably from 0.05 to 0.2% dyestuff/volume of solution.

As already mentioned, the pH conditions depend upon the isoelectric point of the active protein. In general, pH values of from about 2 to about 9 can be considered.

The dissolving of the precipitate requires, as mentioned above, an increase of the pH value above the isoelectric point. In general, therefore, the separated off precipitate is dissolved with a buffer solution with a pH value of from about 4 to about 10. The dyestuff can be removed from the so obtained solution by conventional methods, examples of which include precipitation of the dyestuff by means of polycations, precipitation of the active protein by the addition of salts, such as ammonium sulphate, or of organic solvents, such as acetone, adsorption of the dyestuff on anion exchangers, such as diethylaminoethyl group-containing polymeric carbohydrates or hydrophobic polymers, such as polyvinylpolypyrrolidone, dialysis or ultrafiltration. Appropriate polycations include, for example, the polyethyleneimines.

We have found that the precipitated out active protein-azo dyestuff complex proves to be readily filterable in all cases investigated. Since, in many cases, because of the high selectivity of the process of the precipitation of the desired active protein, precipitations of other proteins and accompanying substances come first, the ease of removal proves to be of especial advantage for the enrichment. The substances precipitating before the desired protein can, because of this property, be easily and completely separated off. The same also applies to the precipitation of the desired active protein itself which, in turn, can easily be separated off by filtration or centrifuging from the impurities still present in the solution.

The present invention also provides an agent for the selective precipitation of biologically active proteins from aqueous solutions thereof without loss of the biological activity, which agent contains or consists of an arylsulphonic acid azo dyestuff with two sulphonate groups, which are separated from one another by 8 to 10 double bonds standing in resonance relationship, amongst which is present at least one N=N double bond.

One preferred agent of this kind contains, as azo dyestuff, 3,3'-(4,4'-biphenylylene-bis-(azo))-bis-(4-amino-1-naphthalenesulphonic acid) and/or a derivative thereof substituted by one or more lower alkyl or lower alkoxy radicals and another preferred agent contains 2,2'-[(diazoamino)-di-p-phenylene]-bis-(7-benzothiazolesulphonic acid) and/or derivatives thereof carrying one or more lower alkyl and/or lower alkoxy radicals.

The present invention provides numerous advantages. Mention has already been made of the relatively small influence on the precipitation of the salt content of the solutions so that even very impure solutions, such as fermentation broths and cell digest solutions, can be treated directly by the process according to the present invention. Furthermore, the process according to the present invention only requires the use of small amounts of precipitation agent and thus, in many cases, avoids the use of the large amounts of organic solvent previously needed for the precipitation. In a typical case, for the preliminary purification of a crude extract, 60% acetone or methanol concentration was previously needed which, in the case of 1000 l. of crude extract, requires the use of 1500 liters of organic solvent. In contradistinction thereto, according to the present invention, it is possible to achieve the precipitation with 1 kg. of dyestuff and, at the same time, also to achieve a substantially better purification, i.e. separation of undesired accompanying substances.

The following Examples are given for the purpose of illustrating the present invention:

EXAMPLE 1

A commercially available, lyophilised crude lipase was dissolved in 0.01 M sodium acetate solution (pH 3.6) to give an activity of about 650 U/ml. To this solution was added 0.3 mg. Congo Red per ml. in the form of a 2% aqueous solution. A precipitate was obtained which contained about 70% of the initial activity, only a small residual activity still being ascertained in the supernatant. The precipitate was filtered off, then washed with the same buffer and again dissolved with buffer at pH 5.0. The dyestuff was then quantitatively precipitated by the dropwise addition of a 10% polyethyleneimine solution. The total activity of the precipitate was thereafter found in the supernatant.

A repetition of this experiment with benzopurpurin 10B gave practically the same results.

EXAMPLE 2

An ascorbate oxidase-containing crude extract in 0.01 M potassium phosphate/acetate buffer (pH 4.6) with a content of ascorbate oxidase of about 20 U/ml. was mixed with 0.4 mg. Congo Red/ml. in the form of a 2% aqueous solution. The resulting precipitate was separated off. 1% residual activity was measured in the supernatant. The precipitate was dissolved with 0.05 M potassium phosphate buffer (pH 7.6). About 60% of the initial activity was found in the solution. The dyestuff can be separated off as described in Example 1.

EXAMPLE 3

Purified cholesterol esterase was taken up in 0.05 M potassium phosphate buffer (pH 4) to give a concentration of about 75 U/ml. The so obtained solution was mixed with 1 mg. Congo Red per ml. of solution and the precipitate formed was separated off. 1% of the initial activity was found in the supernatant, the precipitate containing 99% of the activity. After dissolving the precipitate in 0.1 M potassium phosphate buffer (pH 6), 100% of the activity of the precipitate is again found in the solution.

The process was repeated but with the addition of 0.3 M sodium chloride to the starting solution. The results were unchanged.

EXAMPLE 4

Previously purified peroxidase (POD) with a specific activity of about 100 U/mg. of lyophilisate were dissolved in 0.02 M sodium acetate buffer (pH 3.5) to give a concentration of 100 U/ml. To this solution was added 1 mg. benzopurpurin/ml. in the form of a 1% aqueous solution. The precipitate formed was separated off, 5% of the initial activity of POD remaining in the supernatant. The precipitate was again dissolved with 0.1 M potassium phosphate buffer (pH 7.6). 86% of the initial activity was again found in the solution.

EXAMPLE 5

Phospholipase $A_2$ in the form of a crude extract of the pancreas with a salt content of about 0.1 M was adjusted with acetic acid to pH 4.3. This solution contained 110 U/ml. with a specific activity of about 15 U/mg. protein. The solution was mixed with 2.2 mg. Congo Red/ml. in the form of a 2% solution and the precipitate which appeared was centrifuged off. The supernatant contained 7% of the activity. The precipitate was dissolved with 0.1 M potassium phosphate buffer (pH 7.0) and clarified by precipitation of the dyestuff with polyethyleneimine. After centrifuging, the supernatant contained 92% of the original activity with a specific activity of 55 U/mg. protein.

It will be understood that the specification and examples are illustrative but not limitative of the present invention and that other embodiments within the spirit and scope of the invention will suggest themselves to those skilled in the art.

What is claimed is:

1. Process for the purification or enrichment of a biologically active protein which process comprising mixing an aqueous solution containing the protein at a pH value below its isoelectric point with an arylsulphonic acid azo dyestuff having two sulphonate groups separated from one another by 8 to 10 double bonds in a resonance relationship, including at least one N=N double bond, in sufficient amount result in precipitation of at least the major part of the biological activity of the desired active protein, separating off the precipitate, and bringing the active protein again into solution at a pH value above its isoelectric point.

2. Process as claimed in claimed 1, wherein the azo dyestuff used is 3,3'-(4,4'-biphenylylene-bis(azo))-bis-(4-amino-1-naphthalene-sulphonic acid) or a derivative thereof substituted by one or more lower alkyl or lower alkoxy radicals.

3. Process as claimed in claim 1, wherein the azo dyestuff used is Congo Red (C.I. 22120) or benzopurpurin 10B (C.I. 23560).

4. Process as claimed in claim 1, wherein the azo dyestuff used is 2,2'-[(diazoamino)-di-p-phenylene]-bis-(7-benzothiazolesulphonic acid) or a derivative thereof carrying one or more lower alkyl and/or lower alkoxy radicals.

5. Process as claimed in claim 1, wherein the azo dyestuff used is thiazole yellow G (C.I. 19540).

6. Process as claimed in claim 1, wherein 0.01 to 2.0% wt./vol. of dyestuff is added.

7. Process as claimed in claim 1, wherein the azo dyestuff is used in the form of a 0.05 to 5% solution.

8. Process as claimed in claim 1, wherein the precipitation is carried out at a pH value of from 2 to 9.

9. Process as claimed in claim 1, wherein the separated off precipitate is dissolved with buffer solution with a pH of from 4.5 to 10.

10. Process as claimed in claim 1, wherein, in the solution obtained from the precipitate, the dyestuff is separated from the active protein by the addition of polycations or of an adsorbent.

11. Process as claimed in claim 1, wherein, in the solution obtained from the precipitate, the dyestuff is separated from the active protein by precipitation of the active protein by means of an organic solvent or of a salt or by dialysis or by ultrafiltration.

* * * * *